United States Patent [19]

Into

[11] Patent Number: 4,938,600

[45] Date of Patent: Jul. 3, 1990

[54] METHOD AND APPARATUS FOR MEASURING REGISTRATION BETWEEN LAYERS OF A SEMICONDUCTOR WAFER

[75] Inventor: Stephen W. Into, Billerica, Mass.

[73] Assignee: Interactive Video Systems, Inc., Concord, Mass.

[21] Appl. No.: 308,253

[22] Filed: Feb. 9, 1989

[51] Int. Cl.$^5$ .............................................. G01B 11/00
[52] U.S. Cl. .................................... 356/401; 358/101; 358/106; 358/107; 356/400; 250/491.1
[58] Field of Search ........................ 358/101, 106, 107; 250/491.1; 356/373, 398, 375, 399, 400, 401; 430/22, 30; 324/158 R

[56] References Cited

U.S. PATENT DOCUMENTS

| | | | |
|---|---|---|---|
| 4,467,211 | 8/1984 | Smith et al. | 250/491.1 |
| 4,536,239 | 8/1985 | Benson | 250/491.1 |
| 4,742,233 | 5/1988 | Kuyel | 356/400 |

Primary Examiner—F. L. Evans
Assistant Examiner—Karen P. Hantis
Attorney, Agent, or Firm—Wolf, Greenfield & Sacks

[57] ABSTRACT

Method and apparatus for measuring displacement between layers of a semiconductor wafer wherein systematic errors associated with the measurement system are eliminated. An optical system, including a microscope and a camera, records an image of registration patterns on different layers of the wafer. The image is analyzed to measure displacement between the registration patterns. A first measurement is taken, the wafer is rotated by 180° about the measurement axis, and a second measurement is taken. The actual displacement between layers of the semiconductor wafer is calculated from the first and second measurements. Since the measured displacements change sign when the wafer is rotated and the systematic errors remain constant, systematic errors drop out of the calculated values of actual displacement. System errors can also be calculated for subsequent correction of measured values.

14 Claims, 4 Drawing Sheets

METHOD AND APPARATUS FOR MEASURING REGISTRATION BETWEEN LAYERS OF A SEMICONDUCTOR WAFER

FIELD OF THE INVENTION

This invention relates to methods and apparatus used in the manufacturure of semiconductor wafers and, more particularly, to methods and apparatus for measuring the registration between overlying layers of a semiconductor wafer.

BACKGROUND OF THE INVENTION

The fabrication of complex semiconductor devices involves multiple processing steps which result in multiple patterned layers of different materials being applied to a substrate. The different layers overlie each other and must be accurately registered, or matched in position, to insure proper operation of the device. Displacement between corresponding features on different layers can degrade device performance or can cause the device to be totally inoperative. As used herein, "displacement" between layers of a semiconductor wafer refers to a displacement in the plane of the wafer. As semiconductor devices have become increasingly complex, the dimensions of the features have been correspondingly reduced. This reduction in feature dimensions has reduced acceptable tolerances on displacement between layers. When, for example, the minimum feature size is 2 micrometers, the registration error cannot exceed about 0.1 micrometer.

To assist in registration of overlying layers in semiconductor wafers, it has been common practice to include reqistration patterns or marks in each layer of the wafer. The patterns overlie each other and have a predetermined relationship when the layers are correctly registered. One commonly used registration pattern includes squares of different sizes on the layers to be registered. When the two layers are exactly registered, the squares are concentric. Any registration error produces a displacement of the squares relative to each other.

Since semiconductor wafers including multiple complex integrated circuits are expensive to fabricate, it is usually desirable to verify registration after the application of each layer to the wafer. If the displacement of the layers is outside tolerable limits, the defective layer can, in some cases, be removed and replaced with an accurately reqistered layer. In other cases, the wafer is scrapped, thereby saving the expense of further processing steps on defective wafers.

In the past, it has been common practice to verify registration manually. Experienced operators examine the regqistration of overlying patterns on each wafer. Such techniques are relatively slow and are subject to human error and contamination of the semiconductor wafers.

More recently, automated systems for measuring registration have been developed. In one highly successful registration measurement system, registration errors are measured optically. A video camera records an image of a set of registration patterns through a microscope. The image is processed to obtain a measurement of the registration error.

A measurement system unavoidably introduces certain errors into the measured values. The errors arise both in the optical and the electronic portions of the system and cannot be eliminated entirely. Typically, such errors are systematic, that is, the errors have the same magnitude and direction from measurement to measurement. In the past, it has been customary to calibrate such registration systems by comparing measurements with those obtained from another system, such as a scanning electron microscope, that is known to be accurate. Such calibration techniques are relatively complex and require additional expensive equipment.

It is a general object of the present invention to provide improved methods and apparatus for registration measurement.

It is another object of the present invention to provide methods and apparatus for measuring registration of patterns wherein the effect of systematic errors is eliminated.

It is a further object of the present invention to provide methods and apparatus for determining the systematic errors in a registration measurement system without requiring additional calibration equipment.

It is yet another object of the present invention to provide methods and apparatus for registration measurement which are easy to use.

It is still another object of the present invention to provide methods and apparatus for measuring registration between overlying layers of a semiconductor wafer with high accuracy.

SUMMARY OF THE INVENTION

According to the present invention, these and other objects and advantages are achieved in a method for measuring displacement between a first pattern and a second pattern on a workpiece. The method comprises the steps of positioning the workpiece relative to a measurement apparatus for measurement of the displacement alonq a prescribed measurement direction, making a first measurement of displacement between the first pattern and the second pattern, causing rotation of the workpiece and the measurement apparatus relative to each other by substantially 180° about an axis that is substantially parallel to the measurement direction, making a second measurement of displacement between the first pattern and the second pattern, and determining an actual displacement between the first pattern and the second pattern from the first measurement and the second measurement.

By determining actual displacement from two measurements with the workpiece rotated by 180° between measurements, systematic errors are completely eliminated from the measured values. The step of determining an actual displacement includes the steps of determining an x-axis component, X, of actual displacement according to the equation $X=(X1-X2)/2$ where $X1$ is the x-axis component of the first measurement and $X2$ is the x-axis component of the second measurement, and determining a y-axis component, Y, of actual displacement according to the equation $Y=(Y1-Y2)/2$ where $Y1$ is the y-axis component of the first measurement and $Y2$ is the y-axis component of the second measurement.

The method of the invention can further include the step of determining the systematic errors in the measurement apparatus from the first and second measurements. An x-axis component, A, of error is determined according to the equation $A=(X1+X2)/2$. A y-axis component, B, of error is determined according to the equation $B=(Y1+Y2)/2$. The measured error values can be used to correct subsequent measurements.

In a preferred embodiment, the method of the present invention is used for measuring displacement between layers of a semiconductor wafer. Each layer of the semiconductor wafer is provided with registration patterns. An optical system, including a microscope and a camera, records an image of the patterns. The image is analyzed to measure displacement between the registration patterns. A first measurement is taken, the semiconductor wafer is rotated by 180° and a second measurement is taken. The actual displacement between the layers and systematic errors are determined as described above.

According to another aspect of the invention, there is provided apparatus for measuring displacement between a first pattern and a second pattern on a workpiece. The apparatus comprises measurement means for making first and second measurements of displacement between the first pattern and the second pattern. The first and second measurements are each taken along a prescribed measurement direction. The apparatus further includes means for causing rotation of the workpiece and the measurement means relative to each other after the first measurement and before the second measurement, by substantially 180° about an axis that is substantially parallel to the measurement direction, and means responsive to the first measurement and the second measurement for calculating an actual displacement between the first pattern and the second pattern.

BRIEF DESCRIPTION OF DRAWINGS

For a better understanding of the present invention together with other and further objects, advantages and capabilities thereof, reference is made to the accompanying drawings which are incorporated herein by reference and in which.

DETAILED DESCRIPTION OF THE INVENTION

Figure 1:
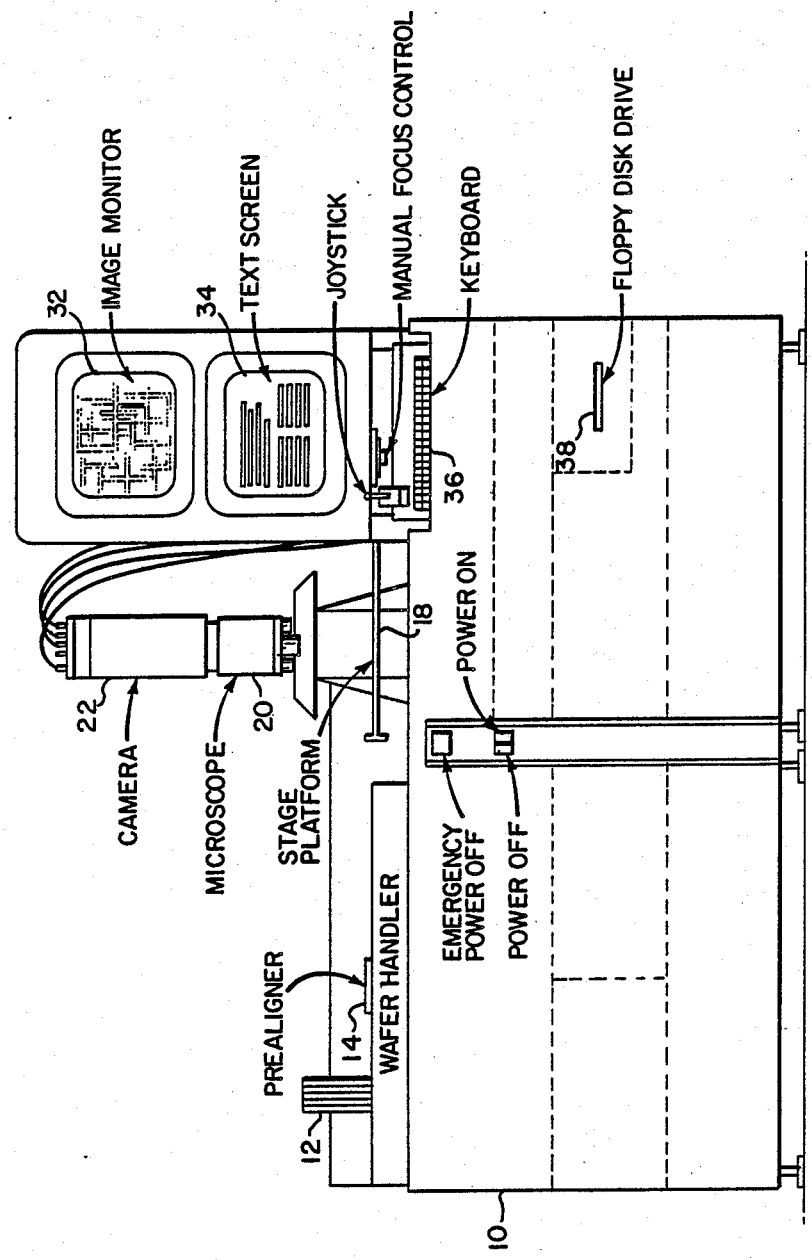
FIG. 1 is an illustration of a registration measurement system suitable for incorporation of the present invention.
Figure 2:
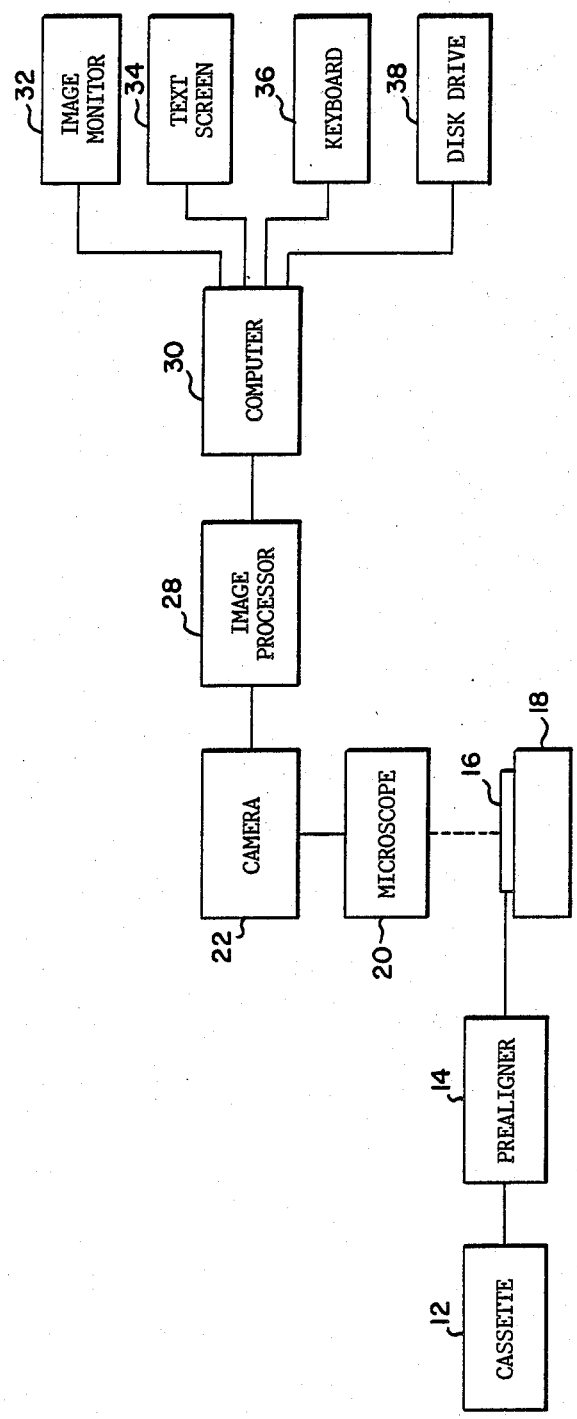
FIG. 2 is a simplified block diagram of the registration measurement system.

An automated system for measuring registration between layers of a semiconductor wafer is illustrated in FIGS. 1 and 2. The major elements of the system, including a wafer handler, an optical system and a computer system, are mounted in a cabinet 10. A cassette wafer holder 12 containing wafers to be measured is mounted on the system. A wafer transport pick (not shown) removes a wafer 16 from the cassette 12 and places it on a prealigner 14. The prealigner 14 rotates the wafer to a predetermined orientation by sensing the wafer flat. The wafer transport pick then transfers the wafer 16 from the prealigner 14 to a measurement stage 18. A suitable wafer handler is a Model CKG1 or CKG3 available from FSI. The stage 18 is movable in three dimensions for positioning selected registration patterns relative to the optical system as described hereinafter.

The optical system includes a microscope 20 and a video camera 22 positioned above the wafer 16. The microscope 20 typically carries several objectives ranging in power from 2.5X to 200X magnification. The wafer 16 is positioned on the stage 18 in a horizontal orientation. The microscope 20 and the camera 22 have a vertical optical axis. The stage 18 is moved until the registration patterns to be measured are located directly under the microscope 20. The microscope turret rotates to the desired objective, and a focused image of the registration patterns is recorded by the camera 22. In an example of the optical system, the microscope 20 is a type Zeiss Axiotron, and the camera 22 is a Dage MT168series camera.

Electrical signals representative of the image are supplied to an image processor 28 and a computer 30. Coupled to the computer 30 are an image monitor 32 for display of the image recorded by the camera 22, a text screen 34 and a keyboard 36 which constitute an input terminal for entering operator commands and a disk drive 38 for storing system software and data. A suitable image processor 28 is available from Recognition Technology, Inc. A suitable computer 30 is a Wyse 386.

The computer 30 processes the siqnals from the camera 22 that represent the image of the registration patterns in order to measure displacement between layers of the semiconductor wafer 16. The wafer 16 includes registration patterns or marks specifically intended to assist in registration. The registration patterns are typically located at multiple sites on the wafer 16.

Figure 3A:
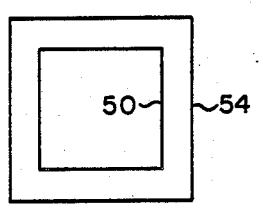
FIGS. 3A and 3B are top and cross-sectional views, respectively, of a typical set of registration patterns.
Figure 3B:
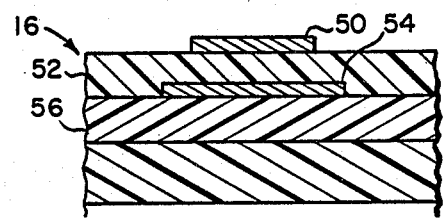

A commonly-used box-in-box registration pattern set is illustrated in FIGS. 3A and 3B. A top view is shown in FIG. 3A, and an enlarged, partial, cross-sectional view of wafer 16 is shown in FIG. 3B. The pattern set includes a square pattern 50 on a first layer 52 of wafer 16 and a square pattern 54 on a second layer 56. The square patterns 50 and 54 have different dimensions. Typically, the patterns 50 and 54 have dimensions on the order of 10–20 micrometers. When layers 52 and 56 are perfectly registered, square patterns 50 and 54 are concentric. When the layers 52 and 56 are not perfectly registered, the patterns 50 and 54 are displaced relative to each other in the plane of the wafer. By measuring the displacement of patterns 50 and 54, the registration between layers 52 and 56 can be quantified.

Figure 3C:
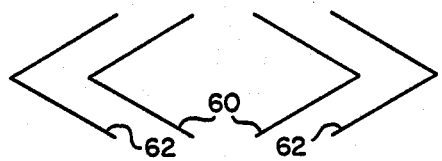
FIG. 3C illustrates an alternative set of registration patterns.

An alternative registration pattern is illustrated in FIG. 3C. Anqled lines 60 are located on a first layer of the semiconductor wafer, and angled lines 62 are located on a second layer. It will be understood that a variety of different registration patterns can be utilized to measure registration.

The measurement of displacement between patterns utilizes known signal processing techniques. The distance between patterns 50 and 54 in FIG. 3A is determined by an analysis of signals from camera 22. The lines of patterns 50 and 54 each produce a transition in a scan line signal from camera 22. The time interval between a transition corresponding to pattern 54 and a transition corresponding to pattern 50 is representative of the distance between the patterns. Signal processing techniques for analyzing the camera image to determine displacement between patterns are well known to those skilled in the art.

In performing registration measurements with a system of the type shown in FIGS. 1 and 2, certain unavoidable errors are introduced by the measuring system. Most of the errors are systematic errors which have the same maqnitude and direction from measurement to measurement. Such errors include, for example, errors due to camera response and image processor response, mechanical errors, optical errors and illumination errors.

In accordance with the present invention, systematic errors are completely eliminated from the measurements without utilizing a known accurate system for calibration or comparison. A first set of displacement measurements is obtained as described above. The displacement between patterns on different layers of the semiconductor device 16 is expressed as an x-axis component and a y-axis component in the plane of wafer 16. The first set of measurements yields measurement values X1, Y1.

After the first measurement, the wafer 16 is rotated by 180° relative to the measurement direction, or axis, which is perpendicular to the plane of measurement. Assuming that the wafer 16 is positioned on stage 18 in a horizontal orientation and that the camera 22 and microscope 20 have a vertical optical axis, the wafer 16 is rotated about a vertical axis parallel to or coincident with the optical axis. However, regardless of the configuration of the system, the wafer is rotated about an axis parallel to or coincident with the measurement axis (an axis perpendicular to the plane of measurement). Rotation of the wafer 16 can be accomplished by rotation of the stage 18. Also, the wafer 16 can be transferred to the prealigner 14, rotated by 180°, and returned to the stage 18. Manual rotation of the wafer 16 is also possible. While rotation of the wafer 16 is usually most practical, the relative rotation can be effected by the optical system so that the image seen by the camera 22 is effectively rotated by 180°.

After rotation of the wafer 16 by 180°, a second set of displacement measurements is obtained. The second set of measurements is made on the same patterns as the first set of measurements. Since the wafer has been reversed, the direction of the displacement between patterns is reversed. If no errors were involved in the measurement, the magnitude of the displacement between patterns would be the same for both measurements. However, since systematic errors in the measurement system do not change direction when the wafer is rotated, the first and second sets of measurements yield different magnitudes.

As demonstrated below, the two sets of measurements can be combined to yield the actual displacement between patterns and values of the systematic errors in the measurement system. Based upon the above discussion, it can be seen that:

$$X1 = +X + A \quad (1)$$

$$X2 = -X + A \quad (2)$$

where
X1 = x-axis component of the first measurement
X2 = x-axis component of the second measurement
X = x-axis component of the actual displacement between patterns
A = total systematic error in X measurement.

Solving equations (1) and (2) for X and A yields:

$$X = (X1 - X2)/2 \quad (3)$$

$$A = (X1 + X2)/2 \quad (4)$$

Similarly, for y-axis measurements:

$$Y1 = +Y + B \quad (5)$$

$$Y2 = -Y + B \quad (6)$$

where
Y1 = y-axis component of first measurement,
Y2 = y-axis component of second measurement,
Y = y-axis component of actual displacement between patterns,
B = systematic error in Y measurement.

Solving equations (5) and (6) for Y and B yields:

$$Y = (Y1 - Y2)/2 \quad (7)$$

$$B = (Y1 + Y2)/2 \quad (8)$$

Figure 4A:
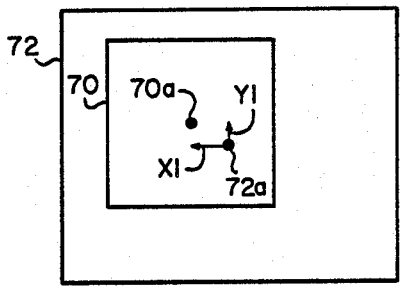
FIGS. 4A and 4B illustrate the measurement technique of the present invention.
Figure 4B:
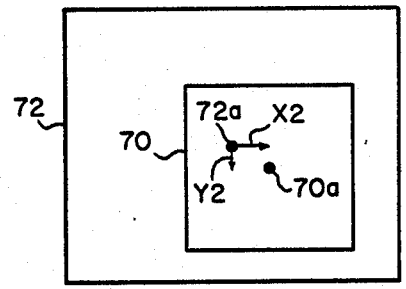

The measurement technique of the present invention is illustrated with reference to FIGS. 4A and 4B. In FIG. 4A, a box-in-box registration pattern set includes a pattern 70 on one level of a semiconductor wafer and a pattern 72 on a second level of the semiconductor wafer. The patterns 70 and 72 are displaced to illustrate the present invention. The center of pattern 70 is shown at 70a, and the center of pattern 72 is shown at 72a. In a first measurement, an x-axis displacement, X1, and a y-axis displacement, Y1, are measured. Patterns 70 and 72 are shown in FIG. 4B after rotation of the wafer by 180°. It can be seen that the direction of displacement between patterns 70 and 72 is reversed. In a second measurement, an x-axis displacement, X2, and a y-axis displacement, Y2, are measured. Because of the rotation of the wafer, X1 and X2 have opposite polarities, and Y1 and Y2 have opposite polarities. By utilizing equations (3), (4), (7) and (8), the actual displacement values X, Y and the total systematic errors A, B are calculated.

The measurement technique of the present invention can be utilized in two principal ways. In one approach, two measurements are taken at each selected pattern site in order to produce actual displacement values at each site. When this approach is used, the first measurements are taken at each selected site on the wafer, the wafer is rotated by 180° and second measurements are then taken at each selected site. The two sets of measurements are used to calculate the actual values of displacement between patterns at each site.

In an alternative approach, the systematic errors are determined initially or periodically. The systematic error values are used to calibrate the system. The measured error values are used to offset, or correct, subsequent displacement measurements.

Figure 5:
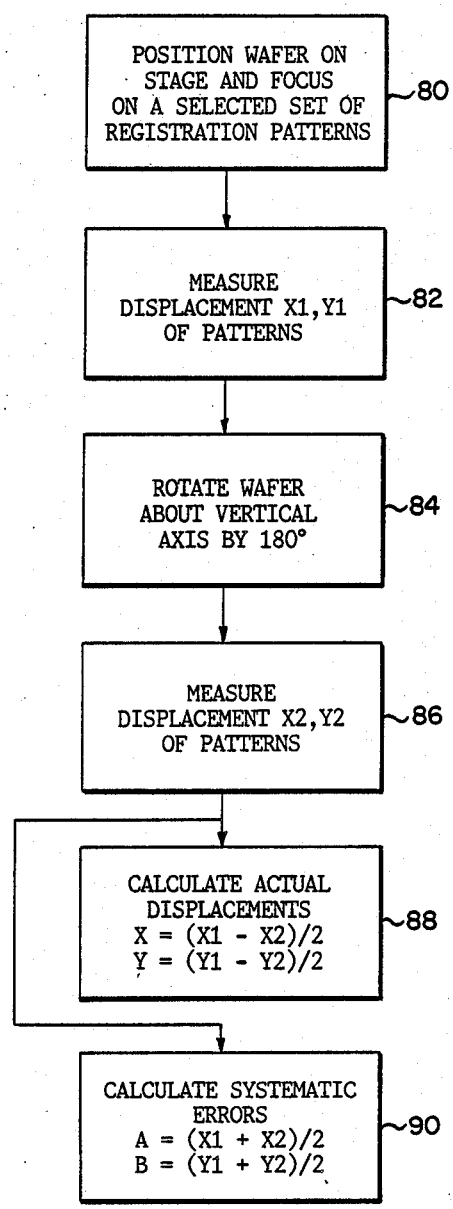
FIG. 5 is a flow diagram illustrating the measurement technique of the present invention.

The measurement technique of the present invention is summarized in a flow diagram in FIG. 5. Initially, a wafer is positioned on stage 16, and the optical system is focused on a selected set of registration patterns in step 80. The displacement X1, Y1 between the selected set of registration patterns is measured in a first measurement step 82. Next, the wafer is rotated about a vertical axis by 180° in step 84. The displacement X2, Y2 between the selected set of patterns is measured in a second measurement step 86. The measured values of displacement are used to calculate actual displacements, X, Y in accordance with equations (3) and (7) in step 88. The systematic errors A, B are calculated in accordance with equations (4) and (8) in step 90.

Table 1 shows sample data taken at five sites on a sample semiconductor wafer with the wafer oriented at 0° and at 180°. Table 1 also shows the measurement errors and the actual displacements derived from the measurement data.

TABLE 1

| | Site Number | 0 Degree | 180 Degree | Measurement Error | Actual Displacement |
|---|---|---|---|---|---|
| X | 1 | −0.71 | 1.37 | 0.33 | −1.04 |
| | 2 | −0.52 | 1.18 | 0.33 | −0.85 |
| | 3 | 0.01 | 0.65 | 0.33 | −0.32 |
| | 4 | 0.23 | 0.43 | 0.33 | −0.10 |
| | 5 | −0.15 | 0.81 | 0.33 | −0.48 |
| | | | | 0.33 average error | |
| Y | 1 | 0.63 | −1.57 | −0.47 | 1.10 |
| | 2 | −0.46 | −0.48 | −0.47 | 0.01 |
| | 3 | −0.13 | −0.81 | −0.47 | 0.34 |
| | 4 | 0.45 | −1.39 | −0.47 | 0.92 |
| | 5 | 0.22 | −1.16 | −0.47 | 0.69 |
| | | | | 0.47 average error | |

The measurement technique of the present invention has been described in connection with measuring reqistration of overlying layers in semiconductor wafers. It will be understood that the technique of the present invention can be used to remove systematic errors in any measurement system where symmetry can be exploited by rotating the workpiece being measured through 180°. The measurement technique of the present invention is applicable to measurement systems other than optical systems including, for example, particle beam systems, scanning laser systems, x-ray systems and backscattering systems.

While there has been shown and described what is at present considered the referred embodiments of the present invention, it will be obvious to those skilled in the art that various changes and modifications may be made therein without departing from the scope of the invention as defined by the appended claims.

What is claimed is:

1. A method for measuring displacement between a first pattern and a second pattern on a workpiece, comprising the steps of:
    positioning the workpiece relative to a measurement apparatus for measurement of said displacement alonq a prescribed measurement direction;
    making a first measurement of displacement between the first pattern and the second pattern;
    causing rotation of the workpiece and the measurement apparatus relative to each other by substantially 180° about an axis that is substantially parallel to the measurement direction;
    making a second measurement of displacement between the first pattern and the second pattern; and
    determining an actual displacement between the first pattern and the second pattern from said first measurement and said second measurement.

2. A method for measuring displacement as defined in claim 1 wherein the step of determining an actual displacement includes the steps of
    determining an x-axis component, X, of actual displacement according to the equation $$X = (X1 - X2)/2$$

where
    X1 = x-axis component of first measurement and
    X2 = x-axis component of second measurement, and
    determining a y-axis component, Y, of actual displacement according to the equation $$Y = (Y1 - Y2)/2$$

where
    Y1 = y-axis component of first measurement and
    Y2 = y-axis component of second measurement.

3. A method for measuring displacement as defined in claim 2 wherein the step of causing relative rotation of the workpiece and the measurement apparatus includes the step of rotating the workpiece by 180°.

4. A method for measuring displacement as defined in claim 2 wherein the steps of making a first measurement of displacement and making a second measurement of displacement each include the step of optically sensing the displacement.

5. A method for measuring displacement as defined in claim 2 further including the step of determining systematic errors in said measurement apparatus from said first measurement and said second measurement.

6. A method for measuring displacement as defined in claim 2 further including the steps of
    determining an x-axis component, A, of error in said first and second measurements according to the equation $$A = (X1 + X2)/2, \text{ and}$$

determining a y-axis component, B, of error in said first and second measurements according to the equation $$B = (Y1 + Y2)/2.$$

7. A method for measuring registration between a first layer and a second layer of a semiconductor wafer, comprising the steps of:
    positioning the wafer for measurement of registration alone a prescribed measurement direction;
    making a first measurement of displacement between a first pattern in said first layer and a second pattern in said second layer;
    rotating the semiconductor wafer by substantially 180° about an axis that is substantially parallel to said measurement direction;
    making a second measurement of displacement between said first pattern and said second pattern; and
    determining an actual displacement between said first pattern and said second pattern from said first measurement and said second measurement.

8. A method for measuring registration as defined in claim 7 wherein the step of determining an actual displacement includes the steps of
    determining an x-axis component, X, of actual displacement according to the equation $$X = (X1 - X2)/2$$

wherein
    X1 = x-axis component of first measurement and
    X2 = x-axis component of second measurement, and
    determining a y-axis component, Y, of actual displacement according to the equation $$Y = (Y1 - Y2)/2$$

where
    Y1 = y-axis component of first measurement and
    Y2 = y-axis component of second measurement.

9. A method for measuring registration as defined in claim 8 further including the steps of determining an x-axis component, A, of error in said first and second measurements according to the equation $$A = (X1 + X2)/2,$$ and determining a y-axis component, B, of error in said first and second measurements according to the equation $$B = (Y1 + Y1)/2.$$

10. Apparatus for measuring displacement between a first pattern and a second pattern on a workpiece, comprising:
   measurement means for making a first measurement of displacement between the first pattern and the second pattern and for making a second measurement of displacement between the first pattern and the second pattern, said first and second measurements each being taken along a prescribed measurement direction;
   means for causing rotation of the workpiece and the measurement means relative to each other after said first measurement and before said second measurement, by substantially 180° about an axis that is substantially parallel to the measurement direction; and
   means responsive to said first measurement and said second measurement for calculating an actual displacement between said first pattern and said second pattern.

11. Apparatus as defined in claim 10 wherein said measurement means includes a microscope and camera means for sensing said first pattern and said second pattern and providing electrical signals representative thereof.

12. Apparatus as defined in claim 11 wherein said calculating means comprises
   means for calculating an x-axis component, X, of actual displacement according to the equation $$X = (X1 - X2)/2$$

where
   X1 = x-axis component of first measurement and
   X2 = x-axis component of second measurement, and means for calculating a y-axis component, Y, of actual displacement according to the equation $$Y = (Y1 - Y2)/2$$

where
   Y1 = y-axis component of first measurement and
   Y2 = y-axis component of second measurement.

13. A method for determining systematic errors in a system for measuring displacement between a first pattern and a second pattern on a workpiece, comprising the steps of:
   positioning the workpiece relative to a measurement apparatus for measurement of said displacement along a prescribed measurement direction;
   making a first measurement of displacement between the first pattern and the second pattern;
   causing rotation of the workpiece and the measurement apparatus relative to each other by substantially 180° about an axis that is substantially parallel to the measurement direction;
   making a second measurement of displacement between the first pattern and the second pattern; and
   determining the systematic errors in the measurement system from said first measurement and said second measurement.

14. A method for measuring systematic errors as defined in claim 13 wherein the step of determining systematic errors includes the steps of
   determining an x-axis component, A, of error according to the equation $$A = (X1 - X2)/2$$

where
   X1 = x-axis component of first measurement and
   X2 = x-axis component of second measurement, and
determining a y-axis component, B, of error according to the equation $$B = (Y1 - Y2)/2$$

where
   Y1 = y-axis component of first measurement and
   Y2 = y-axis component of second measurement.

* * * * *